US012599604B2

(12) United States Patent
Liao et al.

(10) Patent No.: US 12,599,604 B2
(45) Date of Patent: Apr. 14, 2026

(54) APPLICATION OF JAK INHIBITOR IN KIDNEY DISEASE

(71) Applicant: JIANGSU HENGRUI PHARMACEUTICALS CO., LTD., Jiangsu (CN)

(72) Inventors: Cheng Liao, Lianyungang (CN); Lu Su, Lianyungang (CN); Kan Lin, Lianyungang (CN); Jingyang Zhang, Lianyungang (CN)

(73) Assignee: JIANGSU HENGRUI PHARMACEUTICALS CO., LTD., Lianyungang (CN)

( * ) Notice: Subject to any disclaimer, the term of this patent is extended or adjusted under 35 U.S.C. 154(b) by 399 days.

(21) Appl. No.: 18/266,345

(22) PCT Filed: Dec. 10, 2021

(86) PCT No.: PCT/CN2021/137040
§ 371 (c)(1),
(2) Date: Jun. 9, 2023

(87) PCT Pub. No.: WO2022/122010
PCT Pub. Date: Jun. 16, 2022

(65) Prior Publication Data

US 2024/0050433 A1 Feb. 15, 2024

(30) Foreign Application Priority Data

Dec. 11, 2020 (CN) ........................ 202011458342.X

(51) Int. Cl.
*A61K 31/519* (2006.01)
*A61P 13/12* (2006.01)

(52) U.S. Cl.
CPC ............ *A61K 31/519* (2013.01); *A61P 13/12* (2018.01)

(58) Field of Classification Search
CPC .................................................... A61K 31/519
USPC ....................................................... 514/265.1
See application file for complete search history.

(56) References Cited

U.S. PATENT DOCUMENTS

2012/0220652 A1 8/2012 Sporn et al.
2018/0222912 A1 8/2018 Zhang et al.
2019/0060311 A1* 2/2019 Shanler ................ A61K 31/517
2020/0079846 A1 3/2020 Testani et al.
2020/0323832 A1 10/2020 Miao et al.
2021/0292405 A1 9/2021 Kakkar et al.

FOREIGN PATENT DOCUMENTS

CN 101965184 A 2/2011
CN 108026582 A 5/2018
CN 110177549 A 8/2019
CN 110913900 A 3/2020
WO 2013091539 A1 6/2013
WO 2020169783 A1 8/2020

OTHER PUBLICATIONS

Cao, Yu et al., "JAK/STAT Role of JAK/STAT Signaling Pathway in the Progress of Kidney Disease", Chinese Journal of Clinicians (Electronic Edition), vol. 11, No. 1, Jan. 31, 2017 (Jan. 31, 2017), pp. 114-118.
Lakhmir S. Chawla, et al., "Acute kidney disease and renal recovery: consensus report of the Acute Disease Quality Initiative (ADQI) 16 Workgroup", Nat Rev Nephrol. 2017; 13(4): 241-257.
Frank C. Brosius III and John Cijiang He, "JAK Inhibition and Progressive Kidney Disease", Curr Opin Nephrol Hypertens. 2015; 24(1): 88-95.
International Search Report (English and Chinese) and Written Opinion of the ISA (Chinese) issued in PCT/CN2021/137040, mailed Mar. 10, 2022; ISA/CN.
Zhang Lei et al: "Inhibition of JAK2/STAT3 signaling pathway protects mice from the DDP-induced acute kidney injury in lung cancer", Inflammation Research, Birkhaeuser Verslag, Basel, CH, vol. 68, No. 9, Jun. 26, 2019 (Jun. 26, 2019), pp. 751-760, XP036847280, ISSN: 1023-3830, DOI: 10.1007/S000II-019-01258-4.
Vincenti F. et al: "Randomized Phase 2b Trial of Tofacitinib (CP-690,550) in De Novo Kidney Transplant Patients: Efficacy, Renal Function and Safety at 1 Year", American Journal of Transplantation, vol. 12, No. 9, Sep. 1, 2012 (Sep. 1, 2012), pp. 2446-2456, XP093146392, DK ISSN: 1600-6135, DOI: 10.1111/j.1600-6143.2012.04127.x.
Yang N. et al: "Blockage of JAK/STAT signalling attenuates renal ischaemia-reperfusion injury in rats", Nephrology Dialysis Transplantation, vol. 23, No. 1, Aug. 17, 2007 (Aug. 17, 2007), pp. 91-100, XP093146424, GB ISSN: 0931-0509, DOI: 10.1093/ndt/gfm509.
Dimitrova Petya et al: "Inhibition of zymosan-induced kidney dysfunction by tyrphostin AG-490", Journal of Inflammation, Biomed Central, London, GB, vol. 6, No. 1, May 5, 2009 (May 5, 2009), p. 13, XP021050259, ISSN: 1476-9255, DOI: 10.1186/1476-9255-6-13.
Fernando Neria et al: "Inhibition of JAK2 protects renal endothelial and epithelial cells from oxidative stress and cyclosporin A toxicity", Kidney International, vol. 75, No. 2, Jan. 1, 2009 (Jan. 1, 2009), pp. 227-234, XP055603116, GB ISSN: 0085-2538, DOI: 10.1038/ki.2008.487.
P. K. Moore et al., Management of Acute Kidney Injury: Core Curriculum 2018, Am J Kidney Dis. 72(1): 136-148. Published online Feb. 22, 2018. doi: 10.1053/j.ajkd.2017.11.021 © 2018 by the National Kidney Foundation, Inc.

(Continued)

*Primary Examiner* — Raymond J Henley, III
(74) *Attorney, Agent, or Firm* — Harness, Dickey & Pierce, P.L.C.

(57) ABSTRACT

Provided is an application of a JAK inhibitor in kidney disease. Specifically, provided is a use of a JAK inhibitor in the preparation of a drug for treating or preventing kidney disease.

9 Claims, 4 Drawing Sheets

(56) References Cited

OTHER PUBLICATIONS

Cook, Stuart A. and Schafer, Sebastian; Hiding in Plain Sight: Interleukin-11 Emerges as a Master Regulator of Fibrosis, Tissue Integrity, and Stromal Inflammation. DOI: 10.1146/annurev-med-041818-011649. Annual Review of Medicine. Published Jan. 2020.
O'Shea, John J.; et al. The JAK-STAT Pathway: Impact on Human Disease and Therapeutic Intervention. DOI: 10.1146/annurev-med-051113-024537. Annual Review of Medicine. vol. 66. Published 2015.
Acute kidney injury after ruxolitinib: Common complication, uncommon cause. DOI: 10.1002/ajh.25804. AJH Wiley. Published online Apr. 2, 2020.

* cited by examiner

APPLICATION OF JAK INHIBITOR IN KIDNEY DISEASE

CROSS-REFERENCE TO RELATED APPLICATIONS

The present application is a U.S. National Phase Application under 35 U.S.C. 371 of International Application No. PCT/CN2021/137040, filed on Dec. 10, 2021, which claims the right of priority for Chinese patent application 202011458342.X filed on Dec. 11, 2020. The aforementioned Chinese patent application is incorporated herein by reference in its entirety.

TECHNICAL FIELD

The disclosure belongs to the field of medicine, and relates to the application of a JAK inhibitor in kidney disease.

BACKGROUND

In the Kidney Disease: Improving Global Outcomes (KDIGO) guidelines, acute kidney injury (AKI) is defined by an abrupt decrease in kidney function within 7 days, resulting in accumulation of nitrogen-containing products in the blood, with or without a decrease in urine volume. The criteria for AKI are: increase in serum creatinine (Scr) by ≥26.5 μmol/L within 48 h; or increase in Scr to ≥1.5 times baseline, which is known or presumed to have occurred within the prior 7 d; or urine volume <0.5 mL/(kgh) for 6 h. Chronic kidney disease (CKD) is defined as kidney injury for a duration of more than 90 days. AKI and CKD are sometimes interrelated and represent a continuum of the disease process. According to the definition in *Nat Rev Nephrol.* 2017; 13(4): 241-257, the transitional stage from AKI to CKD is referred to as acute kidney disease (AKD).

AKI, AKD and CKD can be considered as a continuous process. Initial kidney injury can lead to persistent kidney injury, eventually leading to CKD. For patients with preexisting CKD, AKI would aggravate the disease of the CKD patients, with AKD existing on a background of CKD. Additionally, the patients are probably at high-risk of kidney disease progression. (See FIG. 1).

The JAK-STAT pathway transmits signals from extracellular ligands, including many cytokines and chemokines. While these responses are best characterized in lymphoid cells, they also occur in kidney cells such as podocytes, mesangial cells, and tubular cells. Enhanced expression and augmented activity of JAK1, JAK2, and STAT3 may promote diabetic nephropathy and their inhibition appears to reduce the disease. In addition, activation of JAK-STAT signaling in autosomal dominant polycystic kidney disease may play an important role in cyst growth (see *Curr Opin Nephrol Hypertens.* 2015; 24(1): 88-95).

For example, baricitinib, a JAK1/2 inhibitor, is clinically demonstrated to have a given efficacy for chronic diabetic nephropathy (NCT01683409); however, there is currently no approved JAK inhibitor drug for the treatment or prevention of kidney disease.

So far, the role of JAK inhibitors in preventing the occurrence of or treating acute kidney disease (AKD) or acute kidney injury (AKI) has not been evaluated.

(3aR,5 s,6aS)—N-(3-methoxy-1,2,4-thiadiazol-5-yl)-5-(methyl(7H-pyrrolo[2,3-d]pyrimidin-4-yl)amino)hexahydrocyclopenta[c]pyrrole-2(1H)-carb oxamide has stronger inhibitory activity against Janus kinase subtype 1 relative to Janus kinase subtype 2 or Janus kinase subtype 3, exhibits specific selectivity for Janus kinase subtype 1, and can provide better safety and effectiveness compared with a pan-JAK inhibitor,

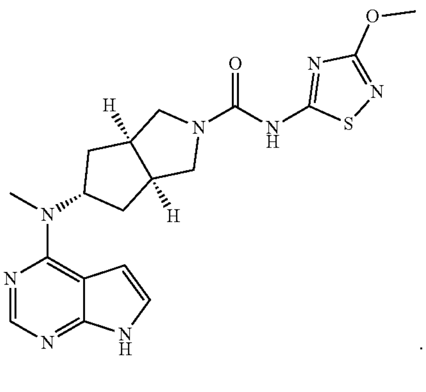 [SMILES: COc1nsc(NC(=O)N2C[C@H]3C[C@H](N(C)c4ncnc5[nH]ccc45)C[C@H]3C2)n1]

.

Content of the Present Invention

The disclosure provides a use in the preparation of a drug for treating or preventing kidney disease, wherein the kidney disease is selected from acute kidney disease (AKD) or acute kidney injury (AKI).

In some embodiments, the JAK inhibitor is selected from tofacitinib, baricitinib, peficitinib, ruxolitinib, delgocitinib, fedratinib, upadacitinib, filgotinib, pacritinib, abrocitinib, PF-06651600, itacitinib, lestaurtinib, PF-06826647, PF-06700841, jaktinib, NS-018, BMS-9115443, gandotinib, INCB-054707, ASN-002, AZD-4205, cerdulatinib, WXFL10203614, CS12192 or a pharmaceutically acceptable salt of the above-mentioned drugs.

In other embodiments, the JAK inhibitor has stronger inhibitory activity against JAK 1 relative to JAK 2 and/or JAK 3, and less than 50%, 40%, 30%, 20%, 10% or 5% of the JAK 2 and/or JAK 3 activity is inhibited.

In other embodiments, the JAK inhibitor is selected from (3aR,5s,6aS)—N-(3-methoxy-1,2,4-thiadiazol-5-yl)-5-(methyl (7H-pyrrolo[2,3-d]pyrimidin-4-yl)amino)hexahydrocyclopenta [c]pyrrole-2(1H)-carboxamide or a pharmaceutically acceptable salt thereof.

The pharmaceutically acceptable salt of the disclosure is selected from but not limited to bisulfate, sulfate, methanesulfonate, maleate, tartrate, succinate, acetate, difluoroacetate, fumarate, citrate, a salt of citric acid, malate, hydrochloride, sulfate, and phosphate.

In other embodiments, the JAK inhibitor is selected from (3aR,5s,6aS)—N-(3-methoxy-1,2,4-thiadiazol-5-yl)-5-(methyl (7H-pyrrolo[2,3-d]pyrimidin-4-yl)amino)hexahydrocyclopenta [c]pyrrole-2(1H)-carboxamide bisulfate.

In view of the serum creatinine (Scr) level, acute kidney disease (AKD) is classified into stage 0, stage 1, stage 2 or stage 3. Stage 0 AKD represents a partial recovery state from AKI; stage OC AKD represents that the serum creatinine level of patients is higher than the baseline level but within 1.5 times the baseline level; stage OB AKD includes the case that the serum creatinine level returns to the baseline level but still with evidence of ongoing kidney injury or reduction of renal reserve capacity; stage OA AKD includes a state in which AKI is pre-existing without kidney structural or injury markers but with a risk of long-term adverse events; patients whose serum creatinine level has not returned to the baseline level and who have kidney structural or injury markers are classified as stage OB/C AKD (see Nat Rev Nephrol. 2017; 13(4): 241-257). In addition, stage 1 AKD includes a serum creatinine level that is 1.5-1.9 times the baseline level; stage 2 AKD includes a serum creatinine level that is 22.9 times the baseline level; stage 3 AKD includes a serum creatinine level that is 3.0 times the baseline level or a serum creatinine level of more than 353.6 μmol/L (≥4.0 mg/dL)** or an ongoing need for renal replacement therapy.

In view of the serum creatinine level, acute kidney injury (AKI) is also classified into four stages: stage 0, stage 1, stage 2 or stage 3. Stage 1 AKI includes a serum creatinine level that is 1.5-1.9 times the baseline level; stage 2 AKI includes a serum creatinine level that is 22.9 times the baseline level; stage 3 AKI includes a serum creatinine level that is 3.0 times the baseline level or a serum creatinine level of more than 353.6 μmol/L (≥4.0 mg/dL)** or an ongoing need for renal replacement therapy (see *Am J Kidney Dis. Jul;* 72(1):136-148).

In some embodiments, the patient with acute kidney injury (AKI) belongs to stage 3 or less. In some embodiments, the patient with acute kidney injury (AKI) belongs to stage 2 or less. In some embodiments, the patient with acute kidney injury (AKI) belongs to stage 1 or less.

In some embodiments, the patient with acute kidney disease (AKD) belongs to stage 3 or less. In some embodiments, the patient with acute kidney disease (AKD) belongs to stage 2 or less. In some embodiments, the patient with acute kidney disease (AKD) belongs to stage 1 or less.

In addition, in the use provided in some embodiments, the kidney disease is selected from but not limited to acute glomerulonephritis, acute interstitial nephritis, idiopathic acute tubulointerstitial nephritis, acute renal insufficiency, pyemia-induced kidney injury, drug-induced kidney injury or surgery-related kidney injury.

The mechanisms of action for drug-induced kidney injury or drug-induced AKI/AKD include: insufficient renal perfusion, toxic and/or ischemic acute tubular necrosis, allergic acute interstitial nephritis, endothelial injury, autoimmune glomerulonephritis, and drug crystal-induced obstruction.

In an alternative embodiment of the disclosure, the JAK inhibitor is administered in a human subject at a dosage selected from 0.5-20 mg, including but not limited to 0.5 mg, 0.6 mg, 0.7 mg, 0.8 mg, 0.9 mg, 1.0 mg, 1.5 mg, 2.0 mg, 2.5 mg, 3.0 mg, 3.5 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, 10.0 mg, 10.5 mg, 11.0 mg, 11.5 mg, 12.0 mg, 12.5 mg, 13.0 mg, 13.5 mg, 14.0 mg, 14.5 mg, 15.0 mg, 15.5 mg, 16.0 mg, 16.5 mg, 17.0 mg, 17.5 mg, 18.0 mg, 18.5 mg, 19.0 mg, 19.5 mg, or 20.0 mg, preferably 1-5 mg.

In some embodiments, the JAK inhibitor is administered in a human subject at a dosage of 1 mg. In some embodiments, the JAK inhibitor is administered in a human subject at a dosage of 2 mg. In some embodiments, the JAK inhibitor is administered in a human subject at a dosage of 4 mg.

The frequency of administration varies with the type and severity of the disease. In an alternative embodiment of the disclosure, the JAK inhibitor is administered with a frequency of once per day, twice per day or three times per day.

In some embodiments, the JAK inhibitor is administered in a human subject at a dosage of 1 mg, once per day.

In some embodiments, the JAK inhibitor is administered in a human subject at a dosage of 2 mg, once per day.

In some embodiments, the JAK inhibitor is administered in a human subject at a dosage of 4 mg, once per day.

In some embodiments, the JAK inhibitor is administered in a human subject at a dosage of 1 mg, twice per day.

The combined routes of administration of the disclosure are selected from oral administration, parenteral administration, and transdermal administration, wherein the parenteral administration includes but is not limited to intravenous injection, subcutaneous injection, and intramuscular injection.

In some embodiments, the JAK inhibitor of the disclosure is administered by oral route.

In another aspect, the disclosure further provides a method for treating or preventing kidney disease, comprising administering to a patient with acute kidney disease or acute kidney injury an effective amount of a JAK inhibitor. In some embodiments, the JAK inhibitor is selected from (3aR, 5 s,6aS)—N-(3-methoxy-1,2,4-thiadiazol-5-yl)-5-(methyl (7H-pyrrolo[2,3-d]pyrimidin-4-yl)amino)hexahydrocyclopenta[c]pyrrole-2(1H)-carboxamide or a pharmaceutically acceptable salt thereof.

In other embodiments, the JAK inhibitor is selected from (3aR,5 s,6aS)—N-(3-methoxy-1,2,4-thiadiazol-5-yl)-5-(methyl (7H-pyrrolo[2,3-d]pyrimidin-4-yl)amino)hexahydrocyclopenta [c]pyrrole-2(1H)-carboxamide bisulfate.

The disclosure further provides a JAK inhibitor use in treating or preventing kidney disease, wherein the kidney disease is selected from acute kidney disease (AKD) or acute kidney injury (AKI). In some embodiments, the JAK inhibitor is selected from (3aR,5 s,6aS)—N-(3-methoxy-1,2,4-thiadiazol-5-yl)-5-(methyl (7H-pyrrolo[2,3-d]pyrimidin-4-yl)amino)hexahydrocyclopenta[c]pyrrole-2(1H)-carboxamide or a pharmaceutically acceptable salt thereof. In other embodiments, the JAK inhibitor is selected from (3aR,5s,6aS)—N-(3-methoxy-1,2,4-thiadiazol-5-yl)-5-(methyl (7H-pyrrolo[2,3-d]pyrimidin-4-yl)amino)hexahydrocyclopenta[c]pyrrole-2 (1H)-carboxamide bisulfate.

Terms

The expression "effective amount" or "therapeutically effective amount" in the disclosure comprises an amount sufficient to alleviate or prevent the symptom or condition of a medical disorder. The "effective amount" also means an amount sufficient to allow or facilitate diagnosis. An effective amount for a particular patient or veterinary subject may vary depending on factors such as the disorder to be treated, the general health of the patient, the method, route and dosage of administration, and the severity of side effects. An effective amount can be the maximal dose or dosing regimen that avoids significant side effects or toxic effects.

DETAILED DESCRIPTION OF THE PREFERRED EMBODIMENT

The disclosure is further described hereinafter in combination with examples, but the examples are not intended to limit the scope of the disclosure.

Compound A: (3 aR,5 s,6aS)—N-(3-methoxy-1,2,4-thiadiazol-5-yl)-5-(methyl(7H-pyrrolo[2,3-d]pyrimidin-4-yl)amino)hexahydrocyclopenta[c]pyrrole-2 (1H)-carb oxamide Compound B: Baricitinib

Example 1: Ischemia-Reperfusion Models

Figure 1:
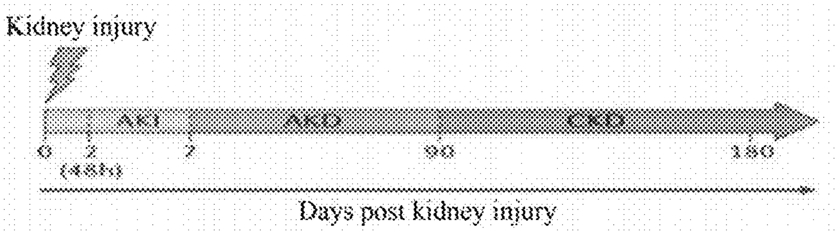
FIG. 1: the continuum of AKI, AKD and CKD post kidney injury.
Figure 2:
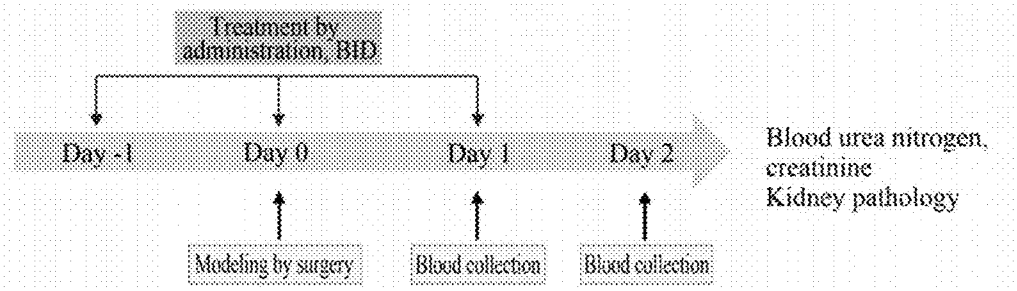
FIG. 2: the experimental process of Example 1.

After arrival and subsequent 7-day acclimation, the animals were randomly grouped. Except the animals in the control group, all other animals needed to be modeled. On day −1, the mice in each group were administered by gavage twice a day (BID). On the day of surgery (day 0), the mice underwent surgery post administration in the morning. On day 1, the dosing was continued, and on day 2, the endpoint treatment was performed. The mice were subjected to blood collection 24 hours and 48 hours post surgery, and for the endpoint treatment, their kidneys were taken and fixed in a formaldehyde solution for subsequent HE pathological detection. The specific experimental process was as shown in FIG. 2.

The specific steps of the ischemia-reperfusion surgery were as follows: the mice were anesthetized with 4% chloral hydrate (10 ml/kg, ip) and secured in a prone position. An incision was made on the back and the right kidney was isolated while ensuring that the adrenal gland and ureter were not injured. The renal artery and renal vein were ligated and the right kidney was excised. The left kidney was isolated, and the renal arterial and venous tracts were carefully separated and clipped for 30 min using a mini bulldog clamp, and then the clamp was loosened. The skin was sutured layer by layer with a needle and thread, and the mice were returned to their cages for recovery.

The mice were administered according to the following dosing regimen, and indicators such as body weight, kidney, blood creatinine and urea nitrogen, and mortality of the mice were observed in each group. The effects of the compounds on the kidney were then evaluated.

| Group | Number (mouse/mice) | Dosage | Route | Frequency |
|---|---|---|---|---|
| Blank group | 6 | 10 mg/kg | Oral administration | BID |
| Model group | 12 | 10 mg/kg | Oral administration | BID |
| Compound A | 12 | 10 mg/kg | Oral administration | BID |
| Compound B | 12 | 10 mg/kg | Oral administration | BID |

Figure 5:
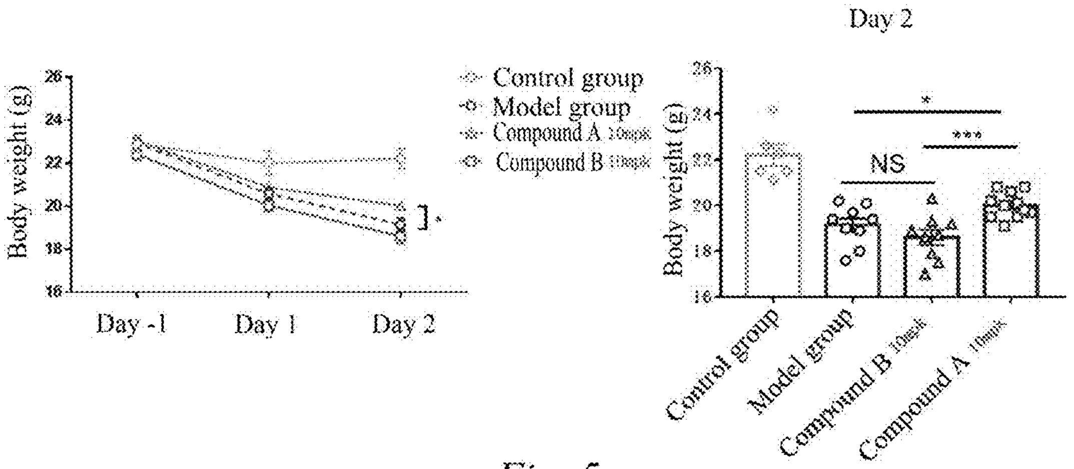
FIG. 5: the body weight curve of mice post ischemia-reperfusion modeling (left) and the body weight of mice in each group on day 2 post modeling (right).
Figure 6:
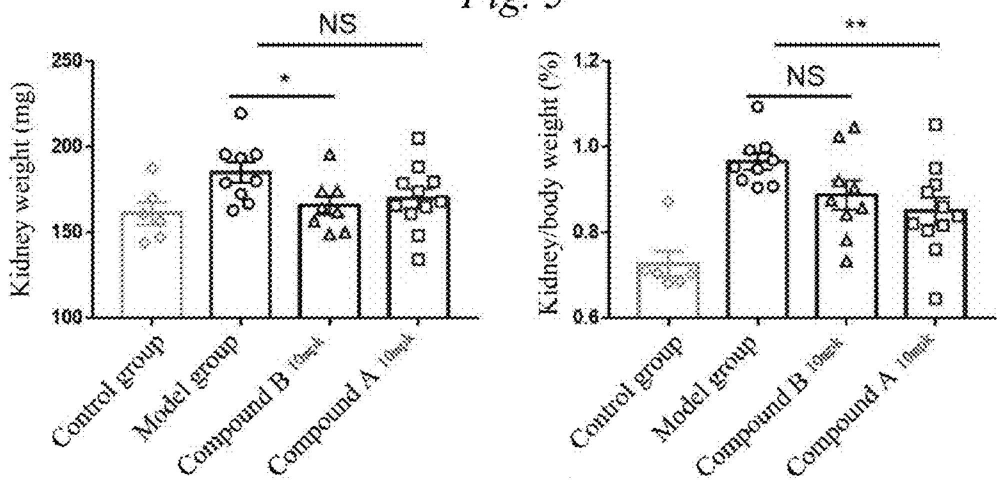
FIG. 6: the kidney weight (left) and kidney/body weight ratio (right) of mice in each group 48 hours post ischemia-reperfusion modeling.

Ischemia-reperfusion modeling resulted in renal compensatory hypertrophy, leading to increased blood creatinine and urea nitrogen levels. With regard to the body weight, the mice in the group administered with 10 mg/Kg (mpk) compound A showed a smaller decrease in body weight, indicating that compound A provided stronger protective effect against body weight reduction caused by ischemia-reperfusion compared with compound B in the administration group of the same dosage (FIG. 5). With regard to the renal compensatory hypertrophy caused by ischemia-reperfusion modeling, the mice in the administration groups showed decreased kidney/body weight ratios, indicating that compound A and compound B could improve the renal compensatory hypertrophy caused by ischemia-reperfusion modeling. In addition, compared with compound B, compound A had some advantages in improving the kidney/body weight ratios of the mice (FIG. 6).

Figure 9:
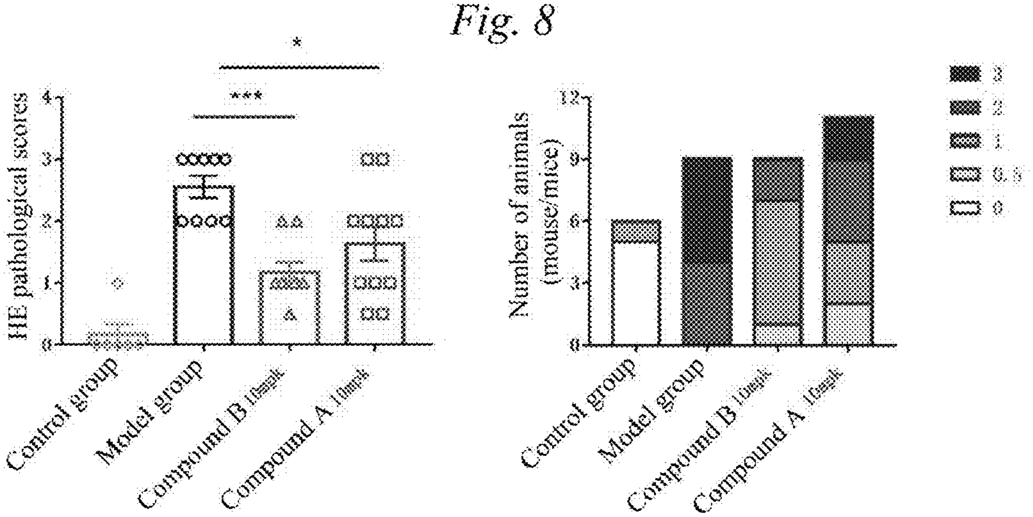
FIG. 9: the scatter diagram of kidney HE pathological scores (left) and the distribution diagram of the number of animals having varying pathological scores (right) in each group of the ischemia-reperfusion mouse models.

With regard to the kidney HE pathological scores, scores 0-3 indicated gradually aggravated pathological grades. Compound A and compound B significantly improved the kidney HE pathological scores in ischemia-reperfusion mouse models (FIG. 9).

Example 2: Ischemia-Reperfusion Models

Ischemia-reperfusion models were established according to the method in Example 1. The mice were administered according to the following dosing regimen, and indicators such as kidney, blood creatinine and urea nitrogen of the mice were observed in groups receiving different dosages.

| Group | Number (mouse/mice) | Dosage | Route | Frequency |
|---|---|---|---|---|
| Blank group | 3 | 10 mg/kg | Oral administration | BID |
| Model group | 8 | 10 mg/kg | Oral administration | BID |
| Compound A | 7 | 2.5 mg/kg | Oral administration | BID |
| Compound A | 7 | 5 mg/kg | Oral administration | BID |
| Compound A | 7 | 10 mg/kg | Oral administration | BID |
| Compound B | 7 | 5 mg/kg | Oral administration | BID |

Figure 7:
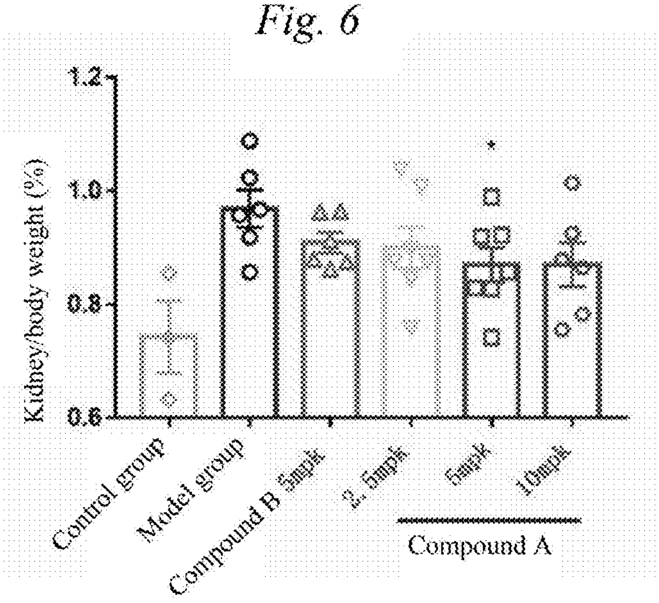
FIG. 7: the kidney/body weight ratio in ischemia-reperfusion mouse models post administration of compound A in each dosage group.

Compound A in all dosage groups (2.5 mpk, 5 mpk and 10 mpk) could reduce the renal hypertrophy caused by ischemia-reperfusion, and there was a significant difference between the 5 mpk compound A administration group and the model group (FIG. 7).

Figure 8:
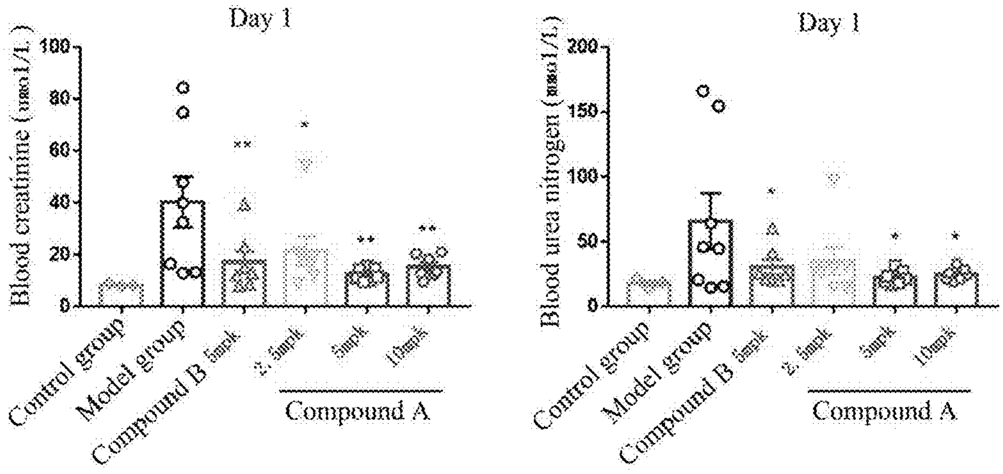
FIG. 8: the blood creatinine (left) and urea nitrogen level (right) in ischemia-reperfusion mouse models.

With regard to the blood creatinine and urea nitrogen, compound A in all dosage groups (2.5 mpk, 5 mpk and 10 mpk) alleviated the increase in blood creatinine and urea nitrogen levels caused by ischemia-reperfusion. Both the 5 mpk and 10 mpk compound administration groups showed significant differences compared with the model group. Furthermore, in the administration groups, compound A demonstrated stronger protective effect compared with compound B at the same dosage (FIG. 8).

Overall, the mice in the administration groups showed significant improvement in the mortality, renal hypertrophy and kidney pathology and alleviation in blood biochemical parameter increase compared with those in the model group, indicating that both compound A and compound B exhibited kidney protective effects. Additionally, compound A exhibited a more excellent kidney protective effect compared with compound B.

Example 3: Lipopolysaccharide (LPS)-Induced Acute Kidney Disease Models

Figure 3:
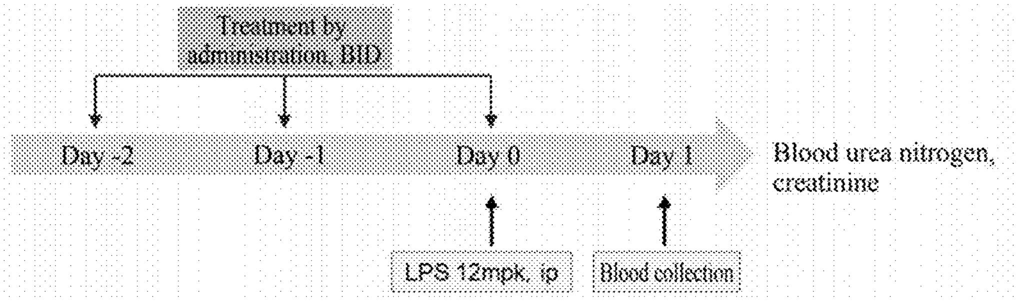
FIG. 3: the experimental process of Example 3.

After arrival and subsequent 7-day acclimation, the animals were randomly grouped. Except the animals in the control group, all other animals needed to be modeled by intraperitoneal injection with LPS. From day −2 to day 0, the mice in each group were administered by gavage, BID. On the day of modeling (day 0), the animals were intraperitoneally injected with LPS (12 mpk) post administration in the morning. Blood samples were collected after 24 h, and creatinine and urea nitrogen levels were measured. The specific experimental process was as shown in FIG. 3.

The mice were administered according to the following dosing regimen, and indicators such as blood creatinine and urea nitrogen of the mice were observed in each group. The effects of the compounds on the kidney were then evaluated.

| Group | Number (mouse/ mice) | Dosage | Route | Fre- quency |
|---|---|---|---|---|
| Blank group | 5 | 10 mg/kg | Oral administration | BID |
| Model group | 10 | 10 mg/kg | Oral administration | BID |
| Compound A | 10 | 2.5 mg/kg | Oral administration | BID |
| Compound A | 10 | 5 mg/kg | Oral administration | BID |
| Compound A | 10 | 10 mg/kg | Oral administration | BID |
| Compound B | 10 | 5 mg/kg | Oral administration | BID |

Figure 10:
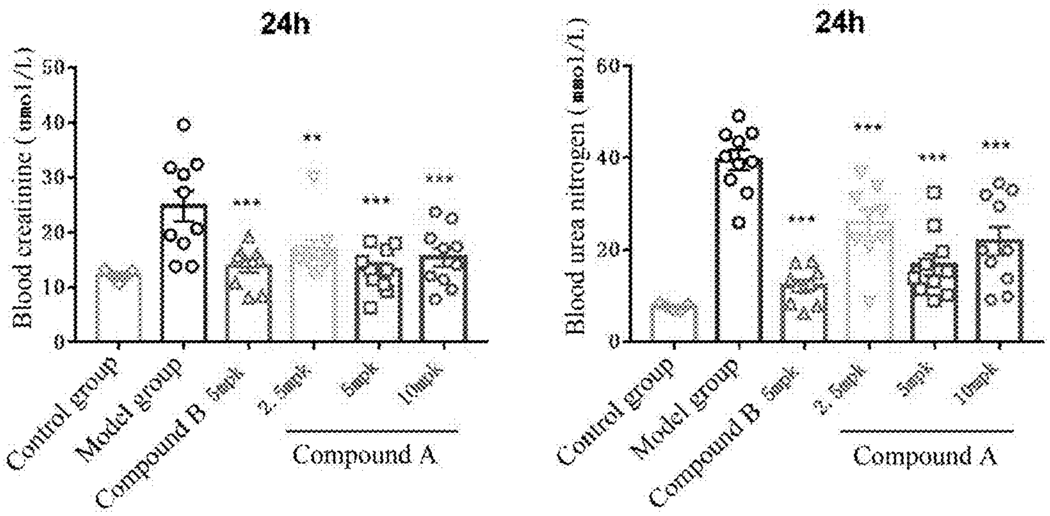
FIG. 10: the blood creatinine (left) and urea nitrogen level (right) in LPS-induced acute kidney injury mouse models.

With regard to the blood creatinine and urea nitrogen levels, in different dosage groups, compound A significantly alleviated the increase in blood creatinine and urea nitrogen levels induced by LPS, and showed significant differences compared with the model group. Stronger kidney protective functions were exhibited in 5 mpk and 10 mpk compound A administration groups compared with 2.5 mpk compound A administration group (FIG. 10). Additionally, compound B also showed a significant difference compared with the model group.

Example 4: Cisplatin-Induced Acute Kidney Disease Models

Figure 4:
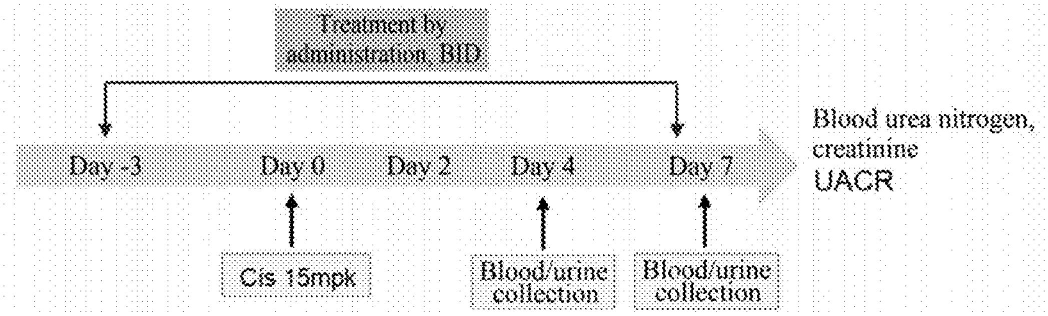
FIG. 4: the experimental process of Example 4.

After arrival and subsequent 7-day acclimation, the animals were randomly grouped. Except the animals in the control group, all other animals needed to be modeled by intraperitoneal injection with cisplatin. From day −3 to day 0, the mice in each group were administered BID. On the day of modeling (day 0), the animals were intraperitoneally injected with cisplatin (15 mg/kg) post administration in the morning. The dosing was continued until day 7. After the modeling, serum and urine samples were collected from the animals on day 4 and day 7, respectively, to measure the blood creatinine, urea nitrogen, and urinary albumin/creatinine (UACR) levels. The specific experimental process was as shown in FIG. 4.

The mice were administered according to the following dosing regimen, and indicators such as blood creatinine and urea nitrogen, and mortality of the mice were observed in each group. The effects of the compounds on the kidney were then evaluated.

| Group | Number (mouse/ mice) | Dosage | Route | Fre- quency |
|---|---|---|---|---|
| Blank group | 5 | 10 mg/kg | Oral administration | BID |
| Model group | 10 | 10 mg/kg | Oral administration | BID |
| Compound A | 10 | 1.25 mg/kg | Oral administration | BID |
| Compound A | 10 | 2.5 mg/kg | Oral administration | BID |
| Compound A | 10 | 5 mg/kg | Oral administration | BID |
| Compound B | 10 | 2.5 mg/kg | Oral administration | BID |

Figure 11:
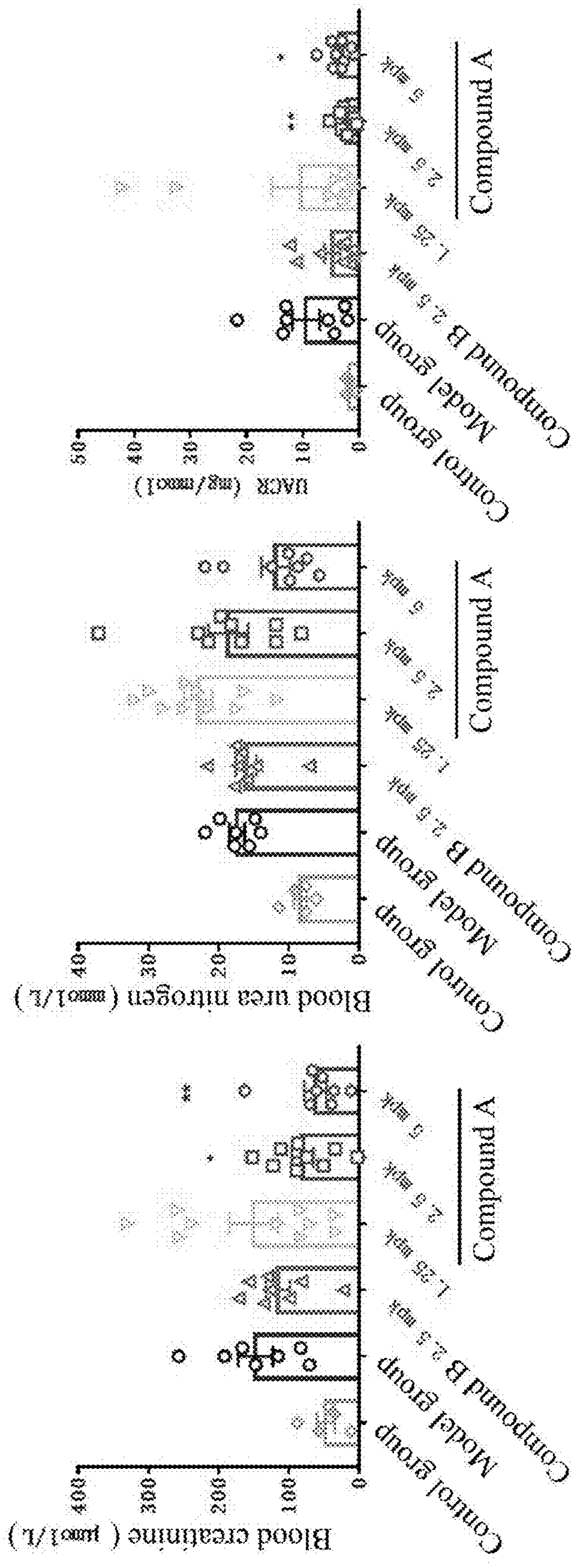
FIG. 11: the blood creatinine (left), blood urea nitrogen (middle), and urinary albumin/creatinine ratio (right) in cisplatin-induced acute kidney injury mouse models.

With regard to the blood creatinine, blood urea nitrogen, and urinary albumin/creatinine ratio, compound A dose-dependently alleviated the increase in blood creatinine and urinary albumin levels induced by cisplatin. The 2.5 mpk and 5 mpk administration groups showed significant differences. Compared with compound B, compound A exhibited stronger kidney protective functions in the cisplatin models (FIG. 11).

With regard to the survival rate of the mice, in the cisplatin-induced model group, all the mice died on day 6 post modeling (100%, 10/10). Compound A at different dosages significantly decreased the mortality of the mice. On day 7 post modeling, the mortality rate of the mice was lower in the compound A administration group compared with the compound B administration group at the same dosage (40% (4/10) vs 80% (8/10)).

Although the specific embodiments of the present disclosure have been described above, it will be understood by those of skill in the art that these are merely illustrative, and that various alterations or modifications can be made to these embodiments without departing from the principle and essence of the present disclosure. Therefore, the scope of protection of the present disclosure is defined by the appended claims.

What is claimed is:

1. A method for treating or preventing kidney disease in a subject in need thereof, the method comprising administering to the subject an effective amount of a JAK inhibitor, wherein the kidney disease is selected from acute kidney disease (AKD) or acute kidney injury (AKI), wherein the JAK inhibitor is (3aR,5s,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole-2(1H)-carboxamide or a pharmaceutically acceptable salt thereof.

2. The method according to claim 1, wherein the pharmaceutically acceptable salt is selected from bisulfate, sulfate, methanesulfonate, maleate, tartrate, succinate, acetate, difluoroacetate, fumarate, citrate, a salt of citric acid, malate, hydrochloride, sulfate, and phosphate.

3. The method according to claim 1, wherein the kidney disease is selected from acute glomerulonephritis, acute interstitial nephritis, idiopathic acute tubulointerstitial nephritis, acute renal insufficiency, drug-induced kidney injury or surgery-related kidney injury.

4. The method according to claim 1, wherein said kidney disease is selected from a patient with acute kidney injury (AKI) below stage 3 or a patient with acute kidney disease (AKD) below stage 3.

5. The method according to claim 1, wherein the JAK inhibitor is administered in a human subject at a dosage of 0.5-20 mg.

6. The method according to claim 1, wherein the JAK inhibitor is administered by oral administration or intravenous injection.

7. The method according to claim 1, wherein the JAK inhibitor is administered with a frequency of once per day, twice per day or three times per day.

8. The method according to claim 1, wherein the JAK inhibitor is administered in a human subject at a dosage of 1-5 mg.

9. The method according to claim 1, wherein the JAK inhibitor is administered in a human subject at a dosage of 1 mg, 2 mg or 4 mg.

* * * * *